United States Patent
Fabian et al.

(10) Patent No.: US 9,125,660 B2
(45) Date of Patent: Sep. 8, 2015

(54) INFLATION AND DEFLATION OF OBSTRUCTION DEVICE

(71) Applicants: Izhak Fabian, Kfar Truman (IL); Nir Altman, Kibbutz Kfar Etzion (IL); Steven Haas, Kochav Yair (IL); Yoav Hirsch, Modiin (IL); Ran Mendelewicz, Herzlia (IL)

(72) Inventors: Izhak Fabian, Kfar Truman (IL); Nir Altman, Kibbutz Kfar Etzion (IL); Steven Haas, Kochav Yair (IL); Yoav Hirsch, Modiin (IL); Ran Mendelewicz, Herzlia (IL)

(73) Assignee: EasyNotes Ltd., Kfar Truman (IL)

( * ) Notice: Subject to any disclaimer, the term of this patent is extended or adjusted under 35 U.S.C. 154(b) by 111 days.

(21) Appl. No.: 13/862,429

(22) Filed: Apr. 14, 2013

(65) Prior Publication Data
US 2014/0309682 A1    Oct. 16, 2014

(51) Int. Cl.
*A61B 17/12* (2006.01)
*A61F 5/00* (2006.01)
*A61B 17/00* (2006.01)

(52) U.S. Cl.
CPC ..... *A61B 17/12136* (2013.01); *A61B 17/12031* (2013.01); *A61B 17/12036* (2013.01); *A61F 5/0033* (2013.01); *A61F 5/0036* (2013.01); *A61F 5/0079* (2013.01); *A61F 5/0089* (2013.01); *A61B 17/1204* (2013.01); *A61B 2017/00818* (2013.01); *A61B 2017/1205* (2013.01)

(58) Field of Classification Search
CPC ......... A61F 2/04; A61M 31/00; A61M 29/00; A61M 25/10; A61M 2025/1054; A61B 6/00; A61B 17/12136; A61K 9/22

USPC ............ 606/192, 191, 194, 195; 604/101.01, 604/101.04, 509, 101.03, 101.05
See application file for complete search history.

(56) References Cited

U.S. PATENT DOCUMENTS

| | | | |
|---|---|---|---|
| 3,411,506 A | 11/1968 | Guevara | |
| 4,598,699 A | 7/1986 | Garran | |
| 4,694,827 A | 9/1987 | Weiner | |
| 5,476,477 A * | 12/1995 | Burns | ............... 606/194 |
| 5,722,986 A * | 3/1998 | Smith et al. | ............... 606/192 |
| 6,558,400 B2 | 5/2003 | Deem | |
| 7,020,531 B1 | 3/2006 | Colliou | |
| 7,060,051 B2 * | 6/2006 | Palasis | ............... 604/101.01 |
| 7,288,099 B2 | 10/2007 | Deem | |

(Continued)

FOREIGN PATENT DOCUMENTS

| | | | |
|---|---|---|---|
| DE | WO 2011/127205 | * 11/2011 | ............... A61F 2/04 |
| WO | 2005/009288 | 2/2005 | |
| WO | 2008/106041 | 9/2008 | |

OTHER PUBLICATIONS

PCT Written Opinion and Search PCT/US2013/072943, Mar. 27, 2014.

*Primary Examiner* — Todd Manahan
*Assistant Examiner* — Majid Jamialahmadi
(74) *Attorney, Agent, or Firm* — Dekel Patent Ltd.; David Klein

(57) ABSTRACT

An assembly including an obstruction device including a proximal obstruction balloon and a distal obstruction balloon mounted on a shaft, the balloons being inflatable via an inflation lumen, and a delivery system that includes an insertion tool and an injection site assembly assembled with one of the balloons, the insertion tool including a connector which is connectable to the injection site assembly and which permits passing tools and injection fluid therethrough.

7 Claims, 3 Drawing Sheets

(56) References Cited

U.S. PATENT DOCUMENTS

| | | |
|---|---|---|
| 7,288,101 B2 | 10/2007 | Deem |
| 7,291,139 B2 * | 11/2007 | Gershowitz ............... 604/509 |
| 7,503,922 B2 | 3/2009 | Deem |
| 7,510,559 B2 | 3/2009 | Deem |
| 7,632,291 B2 * | 12/2009 | Stephens et al. ............. 606/195 |
| 7,803,195 B2 | 9/2010 | Levy |
| 7,862,574 B2 | 1/2011 | Deem |
| 7,909,838 B2 | 3/2011 | Deem |
| 8,075,577 B2 | 12/2011 | Deem |
| 8,080,025 B2 | 12/2011 | Deem |
| 8,226,602 B2 | 7/2012 | Quijana |
| 2004/0019388 A1 | 1/2004 | Starkebaum |
| 2004/0122452 A1 | 6/2004 | Andreas |
| 2005/0273060 A1 | 12/2005 | Levy |
| 2007/0100369 A1 | 5/2007 | Cragg |
| 2007/0149994 A1 | 6/2007 | Sosnowski |
| 2007/0213740 A1 | 9/2007 | Deem |
| 2007/0213748 A1 | 9/2007 | Deem |
| 2007/0250083 A1 | 10/2007 | Deem |
| 2007/0282349 A1 | 12/2007 | Deem |
| 2008/0140099 A1 | 6/2008 | Ghabriel |
| 2008/0319424 A1 * | 12/2008 | Muni et al. .............. 604/890.1 |
| 2008/0319471 A1 * | 12/2008 | Sosnowski et al. .......... 606/192 |
| 2009/0216262 A1 | 8/2009 | Burnett |
| 2010/0256659 A1 | 10/2010 | Aguirre |
| 2010/0274085 A1 | 10/2010 | Mugan |
| 2011/0000496 A1 | 1/2011 | Priplata et al. |
| 2011/0144560 A1 | 6/2011 | Gagner |
| 2011/0152899 A1 | 6/2011 | Deem |
| 2011/0295114 A1 * | 12/2011 | Agah et al. ................ 600/435 |
| 2012/0095385 A1 | 4/2012 | Babkes |
| 2012/0191125 A1 | 7/2012 | Babkes |
| 2012/0265030 A1 | 10/2012 | Li |

* cited by examiner

INFLATION AND DEFLATION OF OBSTRUCTION DEVICE

FIELD OF THE INVENTION

The present invention generally relates to devices for obstructing or reducing flow through a body lumen, in particular for obstructing or reducing flow of gastric contents across the pyloric valve, and a delivery system capable of inflating and deflating balloons of the device.

BACKGROUND OF THE INVENTION

U.S. patent application Ser. No. 13/705,359 describes an obstruction device (also called pyloric plug or just "plug") for obstructing or reducing flow through a body lumen, in particular for obstructing or reducing flow of gastric contents across the pyloric valve (pylorus), as is described more in detail hereinbelow. The device is particularly useful in a transoral gastrointestinal procedure, but the invention is not limited to transoral gastroplasty, and may be used in other laparoscopic, endoscopic, or natural orifice procedures in other body lumens. The plug is designed to be fully operative over a long time, such as but not limited to, between six months and many years. The device can be removed, if desired, and can also be re-implanted.

The plug includes two balloons, one proximal and the other distal, mounted on a shaft. The proximal obstruction balloon is arranged to fit in the stomach, whereas the distal obstruction balloon is arranged to fit in the duodenum. When inflated, both balloons expand towards the pylorus and put pressure from opposite sides on the pylorus, thus fixing the plug in place.

The plug is particularly useful to stop the flow of stomach contents to the proximal gut which includes the duodenum and the initial part of the jejunum. Such a need arises, for example, after creating an alternative path of flow through a gastro-jejunum anastomosis which bypasses the proximal gut. There could be other cases when this need arises, such as after surgery in the duodenum area or in the pancreas or bile outputs to the duodenum. Another indication could be the need to operate endoscopically on the stomach with an inflated stomach. In this case, the plug keeps the inflating air in the stomach and it does not bloat the intestine.

The plug can be used in a method for creating an anastomosis between a stomach and a portion of a small intestine, wherein the plug is used to control passage of stomach contents through the pylorus during and after creation of the anastomosis. For example, before the anastomosis has been created, the plug would allow passage of material therethrough, but after creation of the anastomosis the pylorus plug would either completely block flow (so that material only flows through the anastomosis) or partially block flow (so that material can flow through both the plug and the anastomosis).

SUMMARY OF THE INVENTION

The present invention seeks to provide a delivery system for use with obstruction devices (plugs) that have more than one obstruction balloons, such as, but not limited to, the obstruction device of U.S. patent application Ser. No. 13/705, 359. As is described more in detail hereinbelow, the delivery system is capable of inserting the obstruction device, retrieving it, and inflating and deflating balloons of the obstruction device.

There is thus provided in accordance with an embodiment of the present invention an assembly including an obstruction device including a proximal obstruction balloon and a distal obstruction balloon mounted on a shaft, the balloons being inflatable via an inflation lumen, and a delivery system that includes an insertion tool and an injection site assembly assembled with one of the balloons, the insertion tool including a connector which is connectable to the injection site assembly and which permits passing tools and injection fluid therethrough.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
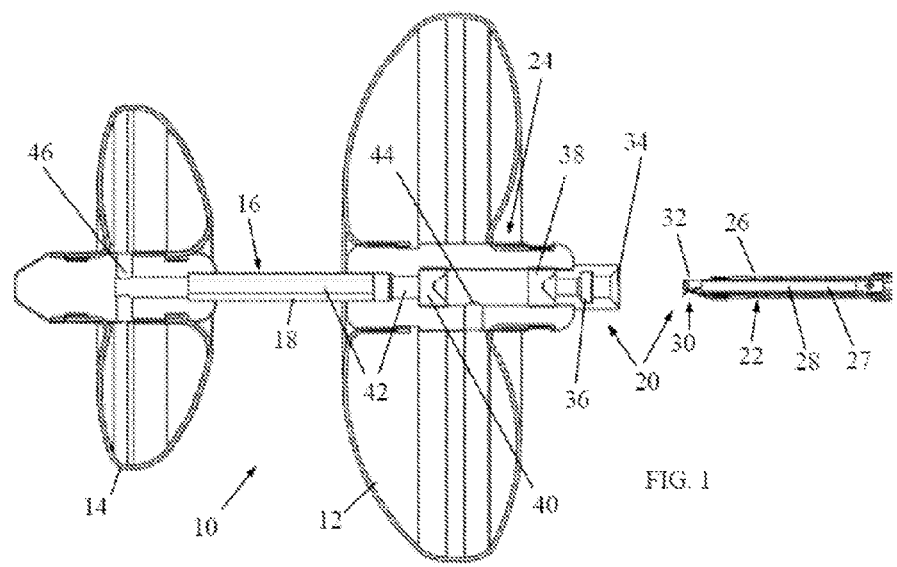
FIG. 1 is a simplified pictorial illustration of an obstruction device and delivery system, constructed and operative in accordance with an embodiment of the present invention.

Reference is now made to FIG. 1, which illustrates an obstruction device (or plug) 10 and delivery system 20, constructed and operative in accordance with an embodiment of the present invention.

Obstruction device 10 includes a proximal obstruction balloon 12 and a distal obstruction balloon 14 mounted on a shaft 16. A portion of shaft 16, referred to as neck 18 or neck portion 18, provides a gap between proximal balloon 12 and distal balloon 14. Neck 18 can have different lengths and thicknesses depending on the application; for example, the dimensions of neck 18 are correlated to the usual width of the pylorus muscle.

The proximal obstruction balloon 12 is arranged to fit in the stomach, whereas the distal obstruction balloon 14 is arranged to fit in the duodenum. When inflated, balloons 12 and 14 expand towards the pylorus and put pressure from opposite sides on the pylorus, thus fixing the plug 10 in place.

Delivery system 20 includes an insertion tool 22 (separate from the plug) and an injection site assembly 24 assembled with one of the balloons, preferably, but not necessarily, the proximal balloon 12. Insertion tool 22 includes a shaft 26 that has a hollow lumen 27 for passing therethrough an inflation tube 28 (tube, catheter or syringe and the like). The distal end of shaft 26 is provided with a connector 30, which connects to injection site assembly 24 and which permits passing injection tools, injection fluid and other tools or substances therethrough.

In one embodiment, connector 30 includes a plurality of resilient fingers 32 (made of a suitable resilient, medically safe material, such as but not limited to, stainless steel, NITINOL or others) which serve as leaf springs.

In one embodiment, injection site assembly 24 includes a proximal insertion port 34 and a distal receiving member 36, wherein the proximal insertion port 34 is of smaller diameter than the distal receiving member 36. Injection site assembly 24 further includes a proximal septum 38, which serves as the proximal injection site 38, and a distal septum 40, which serves as the distal injection site 40, which is axially spaced from the proximal injection site 38. An inflation lumen 42 extends through shaft 16 and is in fluid communication with one or more proximal inflation ports 44 for inflation of proximal balloon 12 and with one or more distal inflation ports 46 for inflation of distal balloon 14.

Figure 2A:
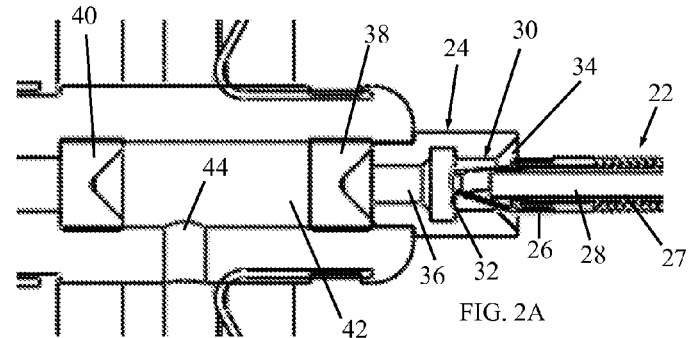
FIGS. 2A and 2B are simplified illustrations of an insertion tool of the delivery system, respectively during and after coupling with the obstruction device, in accordance with an embodiment of the present invention.
Figure 2B:
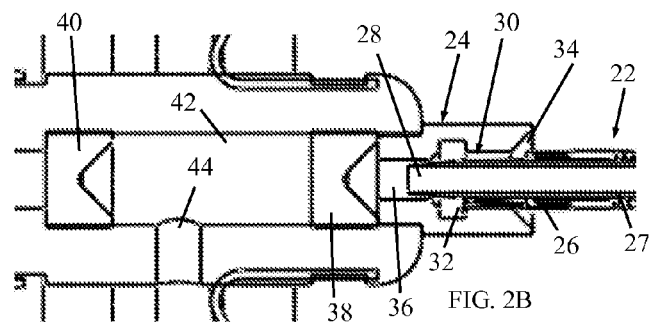

Reference is now made to FIGS. 2A and 2B, which illustrate connecting insertion tool 22 with injection site assembly 24. In FIG. 2A, resilient fingers 32 of connector 30 are inserted into and through the proximal insertion port 34. After passing through the relatively narrow proximal insertion port 34, fingers 32 can expand outwards into the space of distal receiving member 36. As seen in FIG. 2B, inflation tube 28 is inserted through lumen 27 of shaft 26 and presses fingers 32 against the inner surfaces of distal receiving member 36 (which are complementarily shaped in accordance with the shape of fingers 32). Inflation tube 28 can now be advanced distally through proximal injection site 38, as is now explained with reference to FIGS. 3A and 3B.

Figure 3A:
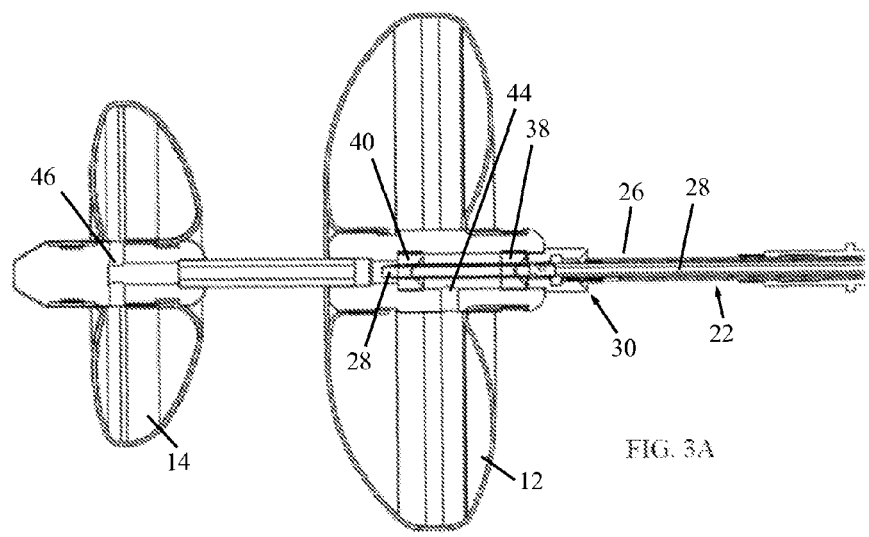
FIGS. 3A and 3B are simplified illustrations of using the delivery system to inflate distal and proximal balloons, respectively, of the obstruction device, in accordance with an embodiment of the present invention.
Figure 3B:
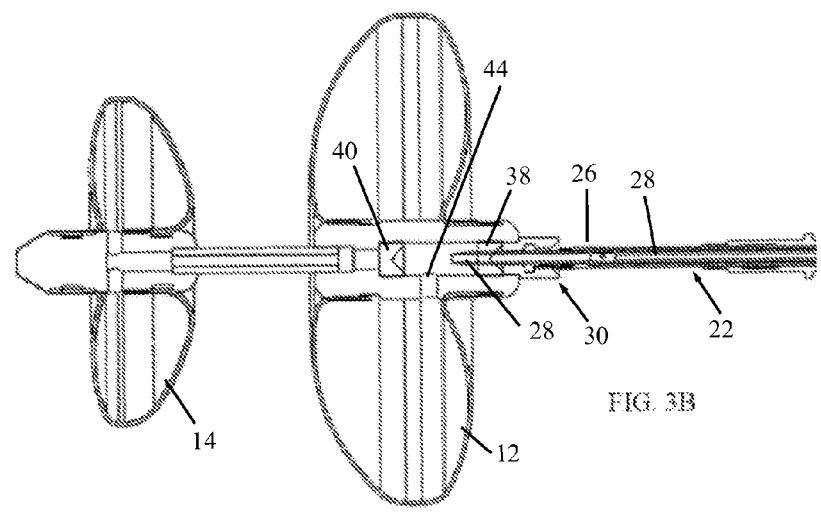

In FIG. 3A, inflation tube 28 has advanced distally through both proximal injection site 38 and distal injection site 40. Distal balloon 14 is inflated with saline, air or other fluid, from a fluid source (not shown) flowing through distal inflation port 46. In FIG. 3B, inflation tube 28 is withdrawn proximally so that distal septum 40 is now sealed and proximal balloon 12 is inflated with fluid flowing through proximal inflation port 44. Optionally, proximal balloon 12 could be inflated first. Each balloon expands in a required direction so that as it expands, it increases pressure on the pylorus.

Both balloons may be deflated by connecting tube 28 to a source of negative pressure (vacuum) and sequentially introducing tube 28 to each injection site; instead of injecting fluid to the balloon, the balloon is emptied by suction. Deflation may instead be done by a deflation mechanism, as is now explained.

Figure 4:
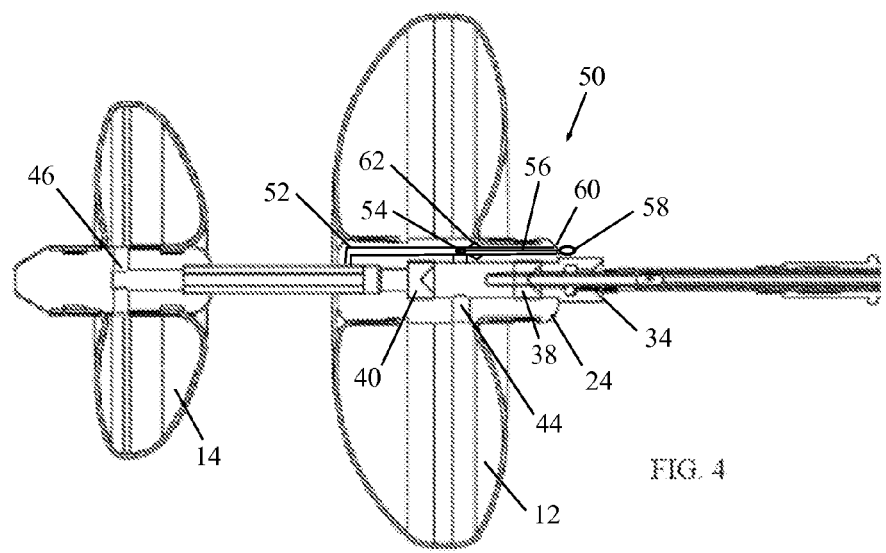
FIG. 4 is a simplified illustration of a deflation mechanism of the delivery system, in accordance with an embodiment of the present invention.

Reference is now made to FIG. 4, which illustrates a deflation mechanism 50 of the delivery system, in accordance with an embodiment of the present invention.

In this embodiment, injection site assembly 24 is formed with a deflation lumen 52 which is in fluid communication with distal inflation port 46, on the distal side of distal septum 40, and with proximal inflation port 44, on the distal side of proximal septum 38. A stopper 54 (e.g., an elastomeric ball) is mounted on a distal end of a slender member 56, which may be provided with a proximal grasping member 58. The slender member 56 is introduced through an outer opening 60 of deflation lumen 52. The slender member 56 may be manipulated with a grasping tool (not shown).

As long as stopper 54 is sealingly seated in proximal inflation port 44, stopper 54 blocks and seals fluid from leaking out of both balloons 12 and 14. When stopper 54 is moved away from proximal inflation port 44, such as to an enlargement 62 in lumen 52, stopper 54 no longer seals the balloons; both balloons 12 and 14 become deflated due to fluid flowing out of them through deflation lumen 52.

In the illustrated embodiment, deflation mechanism 50 deflates both balloons simultaneously. Alternatively, deflation mechanism 50 can be constructed to deflate the balloons one at a time.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An assembly comprising:
    an obstruction device comprising a proximal obstruction balloon and a distal obstruction balloon mounted on a shaft, said balloons being inflatable via an inflation lumen; and
    a delivery system that comprises an insertion tool and an injection site assembly assembled with one of said balloons, said insertion tool comprising a connector which is connectable to said injection site assembly and which permits passing tools and injection fluid therethrough, wherein said insertion tool comprises a shaft that has a hollow lumen; and
    wherein said connector comprises a plurality of resilient fingers insertable into said injection site assembly and the assembly further comprises an inflation tube that passes through said hollow lumen and presses said fingers against inner surfaces of said injection site assembly; and
    wherein said injection site assembly comprises a proximal insertion port and a distal receiving member and wherein said proximal insertion port is narrower than said distal receiving member, and wherein said connector has an operative configuration wherein said resilient fingers are inserted into and through said proximal insertion port, and after passing through said proximal insertion port, said fingers expand outwards into a space of said distal receiving member.

2. The assembly according to claim 1, wherein said injection site assembly comprises a proximal septum, which serves as a proximal injection site, and a distal septum, which serves as a distal injection site and which is axially spaced from said proximal injection site.

3. The assembly according to claim 1, wherein said inflation lumen extends through said shaft of said obstruction device and is in fluid communication with one or more proximal inflation ports for inflation of said proximal balloon and with one or more distal inflation ports for inflation of said distal balloon.

4. The obstruction device according to claim 1, wherein a neck portion of said shaft comprises a gap between said proximal obstruction balloon and said distal obstruction balloon.

5. The obstruction device according to claim 1, wherein said injection site assembly comprises a deflation mechanism operative to deflate said balloons.

6. The obstruction device according to claim 5, wherein said inflation lumen is in fluid communication with one or more proximal inflation ports for inflation of said proximal balloon and with one or more distal inflation ports for inflation of said distal balloon, and wherein said deflation mechanism comprises a deflation lumen formed in said injection site assembly, which is in fluid communication with said distal inflation port and with said proximal inflation port, and wherein a stopper is arranged to be sealingly seated in said proximal inflation port to seal fluid from leaking out of said balloons and to be moved away from said proximal inflation port to permit evacuating fluid from said balloons.

7. A method comprising:
    using an obstruction device comprising a proximal obstruction balloon and a distal obstruction balloon mounted on a shaft, said balloons being inflatable via an inflation lumen, and a delivery system that comprises an insertion tool and an injection site assembly assembled with one of said balloons, said insertion tool comprising a connector which is connectable to said injection site assembly and which permits passing tools and injection fluid therethrough, wherein said insertion tool comprises a shaft that has a hollow lumen, wherein said connector comprises a plurality of resilient fingers insertable into said injection site assembly, and wherein said injection site assembly comprises a proximal insertion port and a distal receiving member, said proximal insertion port being narrower than said distal receiving member;

passing an inflation tube through said hollow lumen so that said resilient fingers are inserted into and through said proximal insertion port, and after passing through said proximal insertion port, said fingers expand outwards into a space of said distal receiving member.

* * * * *